US006234951B1

(12) United States Patent
Hastings

(10) Patent No.: US 6,234,951 B1
(45) Date of Patent: *May 22, 2001

(54) INTRAVASCULAR RADIATION DELIVERY SYSTEM

(75) Inventor: Roger N. Hastings, Maple Grove, MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/782,471

(22) Filed: Jan. 10, 1997

Related U.S. Application Data

(63) Continuation-in-part of application No. 08/608,655, filed on Feb. 29, 1996, now Pat. No. 5,882,290.

(51) Int. Cl.[7] .................................................. A61N 5/00
(52) U.S. Cl. ............................................................... 600/3
(58) Field of Search ........................... 600/1–8; 128/272; 606/194, 191

(56) References Cited

U.S. PATENT DOCUMENTS

| 2,546,761 | 3/1951 | Loftus | 128/1.2 |
|---|---|---|---|
| 2,862,108 | 11/1958 | Meilink | 250/106 |
| 2,955,208 | 10/1960 | Stevens | 250/108 |
| 3,060,924 | 10/1962 | Rush | 128/1.2 |
| 3,147,383 | 9/1964 | Prest | 250/108 |
| 3,324,847 | 6/1967 | Zoumboulis | 128/1.2 |
| 3,505,991 | 4/1970 | Hellerstein et al. | 128/1.1 |

(List continued on next page.)

FOREIGN PATENT DOCUMENTS

| 2166915 | 8/1996 | (CA) . |
|---|---|---|
| 9102312 U | 2/1991 | (DE) . |
| 195 26 680 A1 | 1/1997 | (DE) . |

(List continued on next page.)

OTHER PUBLICATIONS

Tjho–Heslinga et al., "Results of ruthenium irradiation of uveal melanoma", *Radiotherapy Oncology*, vol. 29, pp. 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology*, vol. 232, pp. 482–487, 1994.

(List continued on next page.)

*Primary Examiner*—John P. Lacyk
(74) *Attorney, Agent, or Firm*—Crompton, Seager & Tufte, LLC.

(57) ABSTRACT

An intravascular radiation delivery system including a catheter, a radiation source disposed in an open-ended lumen in the catheter and a closed-ended sheath surrounding the radiation source so as to prevent blood and other fluids from coming into contact with the radiation source. Preferably, the open-ended lumen is centered in the balloon for uniform radiation delivery. The catheter may include a blood perfusion lumen under the balloon or around the balloon. The open-ended lumen in the catheter may have a reduced diameter adjacent the distal end of the catheter to prevent the radiation source from exiting the lumen. Methods of using the radiation delivery system are also disclosed.

An alternative method of delivering radiation to a treatment site inside the vasculature of a patient using a gas-filled balloon catheter and a radiation source disposed in the balloon catheter. The treatment site is exposed to radiation, preferably beta radiation, through the gas-filled balloon.

32 Claims, 8 Drawing Sheets

U.S. PATENT DOCUMENTS

| | | | |
|---|---|---|---|
| 3,643,096 | 2/1972 | Jeffries, Jr. et al. | 250/108 R |
| 3,669,093 | 6/1972 | Sauerwein et al. | 128/1.1 |
| 3,750,653 | 8/1973 | Simon | 128/1.2 |
| 3,811,426 | 5/1974 | Culver et al. | 128/1.2 |
| 3,861,380 | 1/1975 | Chassagne et al. | 128/1.2 |
| 3,866,050 | 2/1975 | Whitfield | 250/497 |
| 3,927,325 | 12/1975 | Hungate et al. | 250/435 |
| 4,096,862 | 6/1978 | DeLuca | 128/348 |
| 4,220,864 | 9/1980 | Sauerwein et al. | 250/497 |
| 4,225,790 | 9/1980 | Parsons, Jr. et al. | 250/497 |
| 4,244,357 | 1/1981 | Morrison | 128/1.2 |
| 4,281,252 | 7/1981 | Parsons, Jr. et al. | 250/497 |
| 4,314,157 | 2/1982 | Gaines | 250/497 |
| 4,364,376 | 12/1982 | Bigham | 128/1.1 |
| 4,584,991 | 4/1986 | Tokita et al. | 128/1.1 |
| 4,588,395 | 5/1986 | Lemelson | 604/59 |
| 4,631,415 | 12/1986 | Sauerwein et al. | 250/497.1 |
| 4,702,228 | 10/1987 | Russell, Jr. et al. | 128/1.2 |
| 4,706,652 | 11/1987 | Horowitz | 128/1.2 |
| 4,763,642 | 8/1988 | Horowitz | 128/1.2 |
| 4,763,671 | 8/1988 | Goffinet | 128/786 |
| 4,782,834 | 11/1988 | Maguire et al. | 128/344 |
| 4,784,116 | 11/1988 | Russel, Jr. et al. | 128/1.2 |
| 4,815,449 | 3/1989 | Horowitz | 600/7 |
| 4,819,618 | 4/1989 | Liprie | 600/7 |
| 4,851,694 | 7/1989 | Rague et al. | 250/497.1 |
| 4,861,520 | 8/1989 | van't Hooft et al. | 252/644 |
| 4,881,937 | 11/1989 | van't Hooft et al. | 600/3 |
| 4,897,076 | 1/1990 | Puthawala et al. | 600/7 |
| 4,936,823 | 6/1990 | Colvin et al. | 600/7 |
| 4,963,128 | 10/1990 | Daniel et al. | 600/7 |
| 4,969,863 | 11/1990 | van't Hooft et al. | 600/3 |
| 4,976,266 | 12/1990 | Huffman et al. | 128/659 |
| 4,976,680 | 12/1990 | Hayman et al. | 600/7 |
| 4,976,690 | 12/1990 | Solar et al. | 604/96 |
| 5,030,194 | 7/1991 | Van't Hooft | 600/3 |
| 5,032,113 | 7/1991 | Burns | 604/96 |
| 5,059,166 | 10/1991 | Fischell et al. | |
| 5,084,001 | 1/1992 | Van't Hooft et al. | 600/3 |
| 5,084,002 | 1/1992 | Liprie | 600/7 |
| 5,092,834 | 3/1992 | Bradshaw et al. | 600/7 |
| 5,103,395 | 4/1992 | Spako et al. | 364/413.26 |
| 5,106,360 | 4/1992 | Ishiwara et al. | 600/2 |
| 5,120,973 | 6/1992 | Rohe et al. | 250/497.1 |
| 5,139,473 | 8/1992 | Bradshaw et al. | 600/3 |
| 5,141,487 | 8/1992 | Liprie | 600/7 |
| 5,147,282 | 9/1992 | Kan | 600/1 |
| 5,163,896 | 11/1992 | Suthanthiran et al. | 600/8 |
| 5,176,617 | 1/1993 | Fischell et al. | |
| 5,183,455 | 2/1993 | Hayman et al. | 600/7 |
| 5,199,939 | 4/1993 | Dake et al. | |
| 5,213,561 | * 5/1993 | Weinstein et al. | 600/7 |
| 5,267,960 | 12/1993 | Hayman et al. | 604/106 |
| 5,282,781 | 2/1994 | Liprie | 600/3 |
| 5,302,168 | 4/1994 | Hess . | |
| 5,308,356 | * 5/1994 | Blackshear, Jr. et al. | 606/194 |
| 5,344,383 | 9/1994 | Liping | 600/3 |
| 5,354,257 | 10/1994 | Roubin et al. | |
| 5,370,685 | 12/1994 | Stevens | 623/2 |
| 5,391,139 | 2/1995 | Edmundson | 600/7 |
| 5,405,309 | 4/1995 | Carden, Jr. | 600/3 |
| 5,409,015 | 4/1995 | Palermo | 128/772 |
| 5,411,466 | 5/1995 | Hess . | |
| 5,425,720 | 6/1995 | Rogalsky et al. | 604/198 |
| 5,429,582 | 7/1995 | Williams | 600/2 |
| 5,484,384 | 1/1996 | Fearnot . | |
| 5,498,227 | 3/1996 | Mawad . | |
| 5,503,613 | 4/1996 | Weinberger . | |
| 5,503,614 | 4/1996 | Liprie | 600/7 |
| 5,532,122 | 7/1996 | Drukier | 435/5 |
| 5,538,494 | 7/1996 | Matsuda | 600/1 |
| 5,540,659 | 7/1996 | Teirstein . | |
| 5,556,389 | 9/1996 | Liprie . | |
| 5,575,749 | 11/1996 | Liprie | 600/3 |
| 5,605,530 | 2/1997 | Fischell et al. . | |
| 5,611,767 | 3/1997 | Williams | 600/2 |
| 5,616,114 | 4/1997 | Thornton et al. . | |
| 5,618,266 | 4/1997 | Liprie . | |
| 5,624,372 | 4/1997 | Liprie | 600/3 |
| 5,643,171 | 7/1997 | Bradshaw et al. | 600/1 |
| 5,649,924 | 7/1997 | Everett et al. | 606/15 |
| 5,653,683 | 8/1997 | D'Andrea | 604/21 |
| 5,662,580 | 9/1997 | Bradshaw et al. | 600/3 |
| 5,674,177 | 10/1997 | Hehrlein et al. | 600/3 |
| 5,683,345 | 11/1997 | Waksman et al. | 600/3 |
| 5,688,220 | 11/1997 | Verin et al. | 600/1 |
| 5,707,332 | 1/1998 | Weinberger | 600/3 |
| 5,720,717 | 2/1998 | D'Andrea | 604/21 |
| 5,722,984 | 3/1998 | Fischell et al. | 606/198 |
| 5,728,042 | 3/1998 | Schwager | 600/3 |
| 5,730,698 | 3/1998 | Fischell et al. | 600/3 |
| 5,782,740 | 7/1998 | Schneiderman | 600/1 |
| 5,782,742 | 7/1998 | Crocker et al. | 600/3 |
| 5,795,286 | 8/1998 | Fischell et al. | 600/3 |
| 5,800,333 | 9/1998 | Liprie | 600/3 |
| 5,803,895 | 9/1998 | Kronholz et al. | 600/3 |
| 5,807,231 | 9/1998 | Liprie | 600/3 |
| 5,816,259 | 10/1998 | Rose | 128/898 |
| 5,816,999 | 10/1998 | Bischoff et al. | 600/3 |
| 5,820,553 | 10/1998 | Hughes | 600/426 |
| 5,833,593 | 11/1998 | Liprie | 600/3 |
| 5,840,008 | 11/1998 | Klein et al. | 600/3 |
| 5,840,009 | 11/1998 | Fischell et al. | 600/3 |
| 5,840,064 | 11/1998 | Liprie | 604/96 |
| 5,843,163 | 12/1998 | Wall | 623/1 |
| 5,851,171 | 12/1998 | Gasson | 600/3 |
| 5,851,172 | 12/1998 | Bueche et al. | 600/7 |
| 5,855,546 | 1/1999 | Hastings et al. | 600/3 |
| 5,857,956 | 1/1999 | Liprie | 600/7 |
| 5,863,284 | 1/1999 | Klein | 600/3 |
| 5,863,285 | 1/1999 | Coletti | 600/3 |
| 5,865,720 | 2/1999 | Hastings et al. | 600/3 |
| 5,871,436 | 2/1999 | Eury | 600/3 |
| 5,871,437 | 2/1999 | Alt | 600/3 |
| 5,873,811 | 2/1999 | Wang et al. | 600/5 |
| 5,879,282 | 3/1999 | Fischell et al. | 600/3 |
| 5,882,290 | 3/1999 | Kume | 600/3 |
| 5,882,291 | 3/1999 | Bradshaw et al. | 600/3 |
| 5,891,091 | 4/1999 | Teirstein | 604/104 |
| 5,897,573 | 4/1999 | Rosenthal et al. | 606/224 |
| 5,899,882 | 5/1999 | Waksman et al. | 604/96 |

FOREIGN PATENT DOCUMENTS

| | | |
|---|---|---|
| 197 54 870 A1 | 6/1998 | (DE) . |
| 197 24 223 C1 | 12/1998 | (DE) . |
| 93203354 | 12/1990 | (EP) . |
| 0 514 913 A2 | 11/1992 | (EP) . |
| 93110531 | 7/1993 | (EP) . |
| 94109858 | 6/1994 | (EP) . |
| 0 633 041 A1 | 1/1995 | (EP) . |
| 0 686 342 A1 | 12/1995 | (EP) . |
| 0 688 580 A1 | 12/1995 | (EP) . |
| 0 749 764 A1 | 12/1996 | (EP) . |
| 0 754 472 A2 | 1/1997 | (EP) . |
| 0 754 473 A2 | 1/1997 | (EP) . |
| 0 593 136 B1 | 3/1997 | (EP) . |
| 0 696 906 B1 | 4/1997 | (EP) . |
| 0 778 051 A1 | 6/1997 | (EP) . |
| 0 801 961 A2 | 10/1997 | (EP) . |

| | | |
|---|---|---|
| 0 813 894 A2 | 12/1997 | (EP) . |
| 0 629 380 B1 | 7/1998 | (EP) . |
| WO 86/03124 | 6/1986 | (WO) . |
| PCT/US92/ 07447 | 9/1992 | (WO) . |
| WO 93/04735 | 3/1993 | (WO) . |
| PCT/EP94/ 01373 | 4/1994 | (WO) . |
| PCT/US94/ 04857 | 5/1994 | (WO) . |
| PCT/US95/ 13728 | 10/1994 | (WO) . |
| WO 94/25106 | 11/1994 | (WO) . |
| WO 94/26205 | 11/1994 | (WO) . |
| WO 95/07732 | 3/1995 | (WO) . |
| 9519807 * | 7/1995 | (WO) .................................... 600/3 |
| PCT/US95/ 14133 | 11/1995 | (WO) . |
| PCT/DE96/ 00042 | 1/1996 | (WO) . |
| WO 96/06654 | 3/1996 | (WO) . |
| WO 96/10436 | 4/1996 | (WO) . |
| WO 96/13303 | 5/1996 | (WO) . |
| WO 96/14898 | 5/1996 | (WO) . |
| WO 96/17654 | 6/1996 | (WO) . |
| WO 96/22121 | 7/1996 | (WO) . |
| WO 96/29943 | 10/1996 | (WO) . |
| WO 96/40352 | 12/1996 | (WO) . |
| WO 97/07740 | 3/1997 | (WO) . |
| WO 97/09937 | 3/1997 | (WO) . |
| WO 97/18012 | 5/1997 | (WO) . |
| WO 97/19706 | 6/1997 | (WO) . |
| WO 97/25102 | 7/1997 | (WO) . |
| WO 97/25103 | 7/1997 | (WO) . |
| WO 97/40889 | 11/1997 | (WO) . |
| WO 98/01183 | 1/1998 | (WO) . |
| WO 98/01184 | 1/1998 | (WO) . |
| WO 98/01185 | 1/1998 | (WO) . |
| WO 98/01186 | 1/1998 | (WO) . |
| WO 98/16151 | 1/1998 | (WO) . |
| WO 98/11936 | 3/1998 | (WO) . |
| WO 98/20935 | 5/1998 | (WO) . |
| WO 98/25674 | 6/1998 | (WO) . |
| WO 98/29049 | 7/1998 | (WO) . |
| WO 98/30273 | 7/1998 | (WO) . |
| WO 98/34681 | 8/1998 | (WO) . |
| WO 98/36788 | 8/1998 | (WO) . |
| WO 98/36790 | 8/1998 | (WO) . |
| WO 98/36796 | 8/1998 | (WO) . |
| WO 98/39052 | 9/1998 | (WO) . |
| WO 98/39062 | 9/1998 | (WO) . |
| WO 98/39063 | 9/1998 | (WO) . |
| WO 98/40032 | 9/1998 | (WO) . |
| WO 98/46309 | 10/1998 | (WO) . |
| WO 98/55179 | 12/1998 | (WO) . |
| WO 98/57706 | 12/1998 | (WO) . |
| WO 99/01179 | 1/1999 | (WO) . |
| WO 99/02219 | 1/1999 | (WO) . |
| WO 99/04706 | 2/1999 | (WO) . |
| WO 99/04856 | 2/1999 | (WO) . |
| WO 99/10045 | 3/1999 | (WO) . |

OTHER PUBLICATIONS

*Radiotherapy of Intraocular and Orbital Tumors*, Springer–Verlak publishers, Berlin Heidelberg and New York, copyright 1993, pp. 23–30 and 363–367.

Fackelmann, "Harbinger of a Heart Attack", *Science News*, vol. 151, Jun. 14, 1997, pp. 374–375.

Raloff, "Nuclear Medicine Gets Friendlier—Experimental Therapies Seek to Poison Just the Disease", *Science News*, vol. 152, Jul. 19, 1997, pp. 40–41.

Sutherland, "Managing Cancer Through Synergy", *Administrative Radiology Journal*, Nov. 1996, pp. 21–27.

* cited by examiner

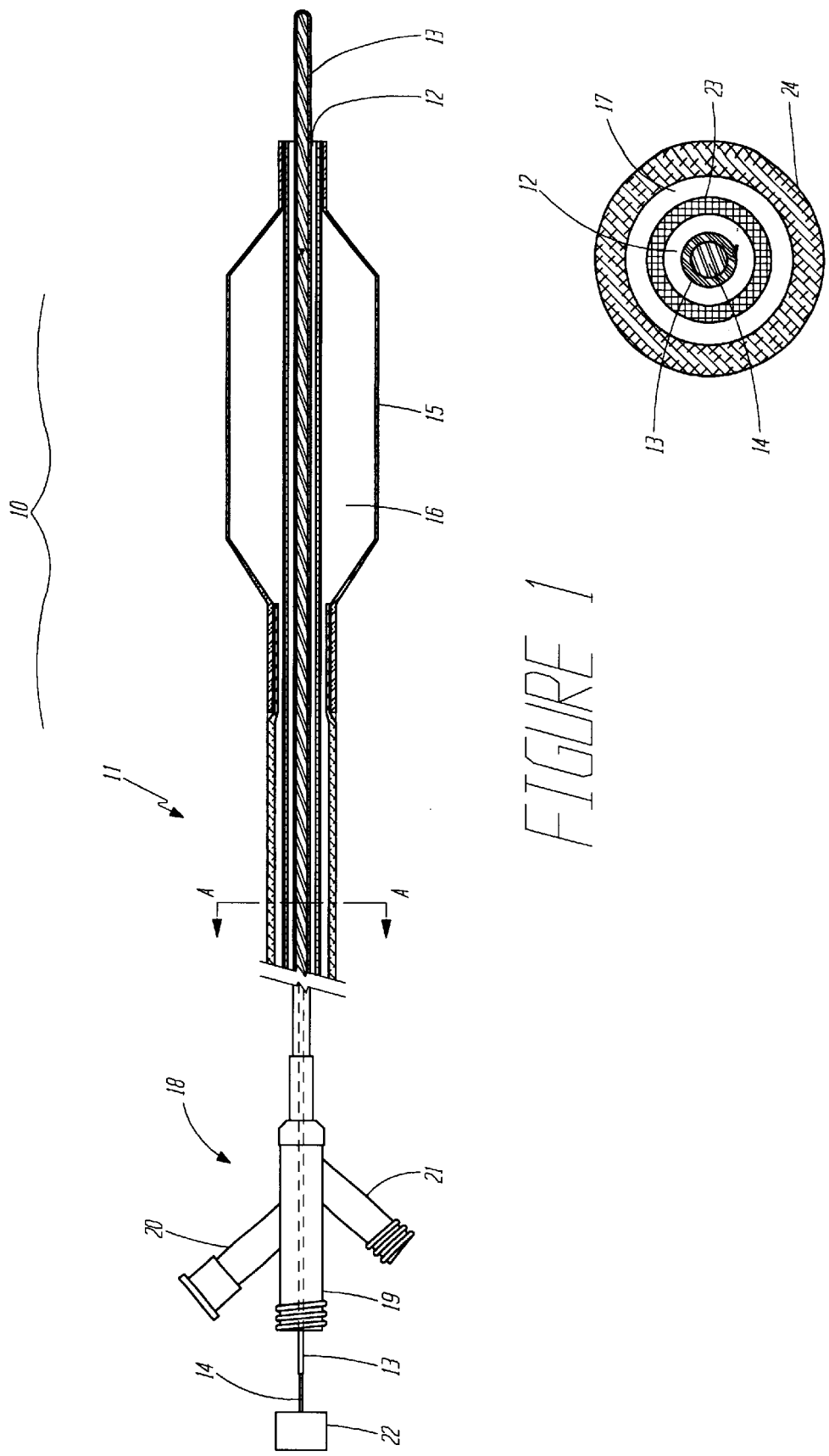

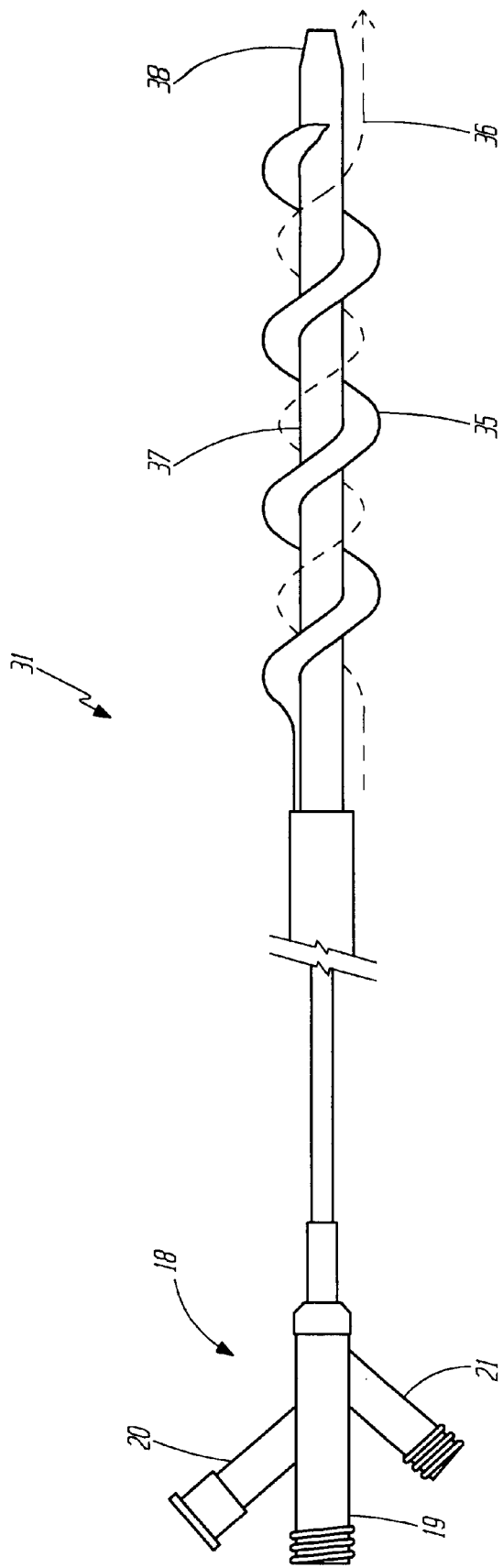

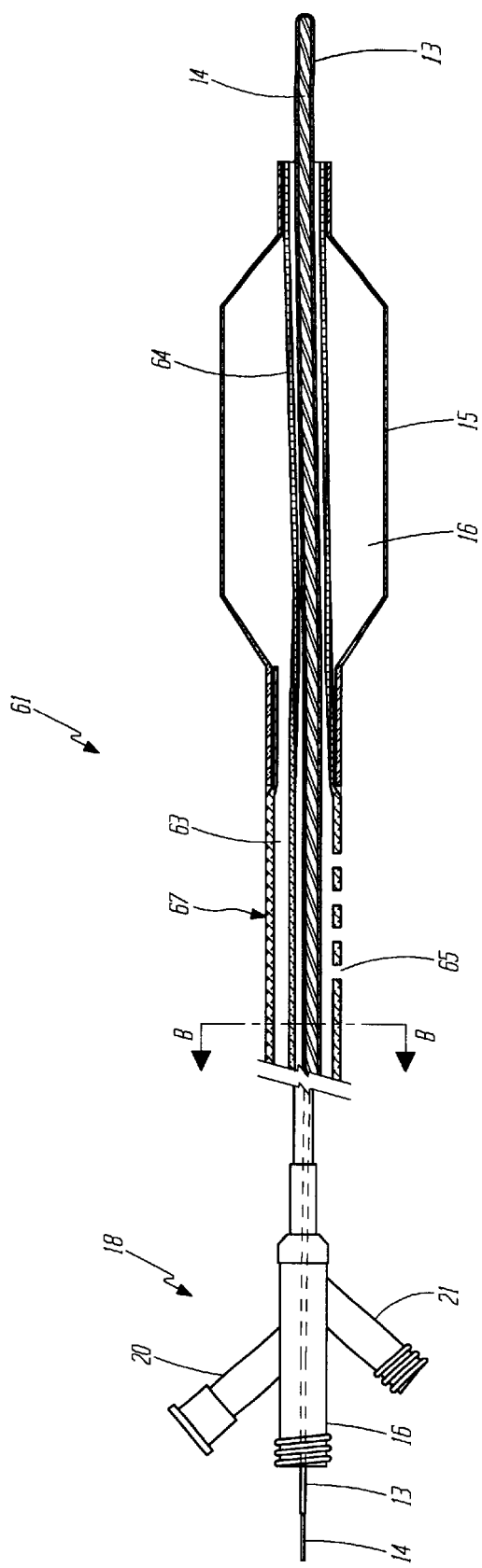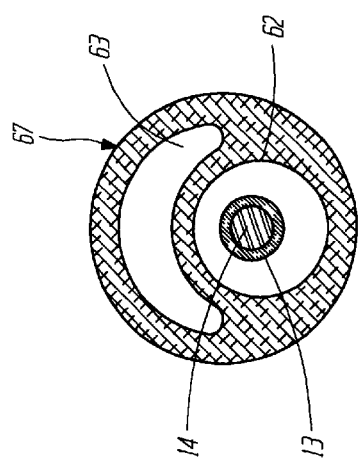
FIGURE 6
FIGURE 7

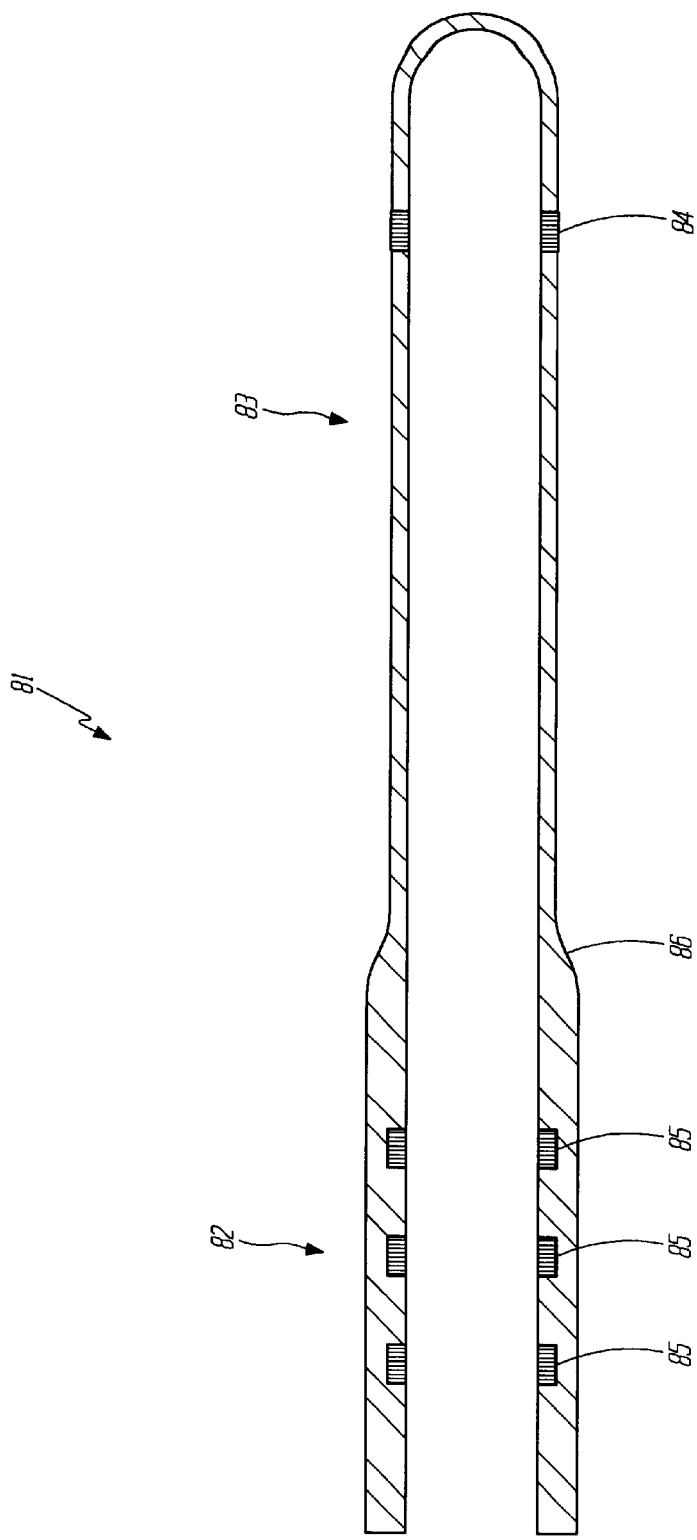

INTRAVASCULAR RADIATION DELIVERY SYSTEM

CROSS-REFERENCE TO RELATED APPLICATIONS

This application is a continuation-in-part of U.S. patent application Ser. No. 08/608,655 filed on Feb. 29, 1996 now U.S. Pat. No. 5,882,290 entitled INTRAVASCULAR RADIATION DELIVERY SYSTEM, the entire disclosure of which is incorporated herein by reference.

FIELD OF THE INVENTION

The present invention generally relates to intralumenal devices used to deliver radiation inside a living body. More specifically, the present invention relates to intravascular devices used to deliver radiation inside the vasculature of a patient for therapeutic purposes. Those skilled in the art will recognize the benefits of applying the present invention to similar fields not discussed herein.

BACKGROUND OF THE INVENTION

Intravascular diseases are commonly treated by relatively non-invasive techniques such as percutaneous translumenal angioplasty (PTA) and percutaneous translumenal coronary angioplasty (PTCA). These therapeutic techniques are well-known in the art and typically involve the use of a balloon catheter with a guide wire, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. For example, the restriction may redevelop over a period of time, a phenomenon commonly referred to as restenosis. Various theories have been developed to explain the cause for restenosis. It is commonly believed that restenosis is caused, at least in part, by cellular proliferation over a period of time to such a degree that a stenosis is reformed in the location of the previously dilated restriction.

Intravascular radiation, including thermal, light and radioactive radiation, has been proposed as a means to prevent or reduce the effects of restenosis. For example, U.S. Pat. No. 4,799,479 to Spears suggests that heating a dilated restriction may prevent gradual restenosis at the dilation site. In addition, U.S. Pat. No. 5,417,653 to Sahota et al. suggests that delivering relatively low energy light, following dilatation of a stenosis, may inhibit restenosis. Furthermore, U.S. Pat. No. 5,199,939 to Dake et al. suggests that intravascular delivery of radioactive radiation may be used to prevent restenosis. While most clinical studies suggest that thermal radiation and light radiation are not significantly effective in reducing restenosis, some clinical studies have indicated that intravascular delivery of radioactive radiation is a promising solution to the restenosis enigma.

Since radioactive radiation prevents restenosis but will not dilate a stenosis, radiation is preferably administered during or after dilatation. European Patent No. 0 688 580 to Verin discloses a device and method for simultaneously dilating a stenosis and delivering radioactive radiation. In particular, Verin '580 discloses balloon dilatation catheter having an open-ended lumen extending therethrough for the delivery of a radioactive guide wire.

One problem associated with the open-ended lumen design is that bodily fluids (e.g., blood) may come into contact with the radioactive guide wire. This may result in contamination of the bodily fluid and require the resterilization or disposal of the radioactive guide wire. To address these issues, U.S. Pat. No. 5,503,613 to Weinberger et al. proposes the use of a separate closed-ended lumen in a balloon catheter. The closed-ended lumen may be used to deliver a radioactive guide wire without the risk of contaminating the blood and without the need to resterilize or dispose of the radiation source.

The closed-ended lumen design also has draw backs. For example, the addition of a separate delivery lumen tends to increase the overall profile of the catheter. An increase in profile is not desirable because it may reduce flow rate of fluid injections into the guide catheter and it may interfere with navigation in small vessels.

Another problem with both the open-ended and closed-ended devices is that radiation must travel through the fluid filled balloon in order to reach the treatment site. While this is not a problem for gamma radiation, it poses a significant problem for beta radiation which does not penetrate as well as gamma radiation. Beta radiation is considered a good candidate for radiation treatment because it is easy to shield and control exposure. In larger vessels (e.g., 0.5 cm or larger), a fluid filled balloon absorbs a significant amount of beta radiation and severely limits exposure to the treatment site.

SUMMARY OF THE INVENTION

The present invention overcomes these problems by providing a radiation delivery system that permits the use of an open-ended delivery lumen without the risk of blood contamination and without the need to dispose of or resterilize the radiation source. In addition, the present invention provides a radiation delivery system that permits beta radiation to be delivered through a balloon without a significant decrease in radiation exposure to the treatment site, even in large vessels.

One embodiment of the present invention may be described as a catheter having an open-ended lumen, a radiation source disposed in the open-ended lumen of the catheter and a closed-end sheath surrounding the radiation source. The closed-end sheath prevents blood and other fluids from coming into contact with the radiation source so that blood is not contaminated and the radiation source may be reused. The catheter may be a balloon catheter and may include a guide wire disposed in the open-ended lumen of the catheter. The open-ended lumen may be a full-length lumen or a partial-length lumen (e.g., a rapid exchange lumen). Preferably, the lumen is centered in the balloon for uniform radiation delivery. The catheter may also include a blood perfusion lumen under the balloon or around the balloon. The open-ended lumen in the catheter may have a reduced diameter adjacent the distal end of the catheter to prevent the radiation source from exiting the lumen. Alternatively, the closed-end sheath may have a ridge which abuts a corresponding restriction in the open-end lumen of the catheter to prevent the radiation source from exiting the lumen.

Another embodiment of the present invention may be described as a method of delivering radiation to a treatment site inside the vasculature of a patient using a the radiation delivery system described above wherein the method includes the steps of (1) inserting the catheter into the vasculature of a patient; (2) inserting the radiation source into the closed-end sheath; (3) inserting the radiation source and the closed-end sheath into the lumen of the catheter such that the radioactive portion is positioned adjacent a treatment site; and (3) exposing the vascular wall to radiation from the radiation source. Alternatively, the sheath nay be inserted into the catheter before the radiation source is loaded into the sheath. The method may also include the steps of (4) removing the radiation source from the catheter; and (5) removing the catheter from the patient. The catheter may be inserted into the vasculature over a guide wire and the guide wire may be removed from the catheter prior to exposing the vascular wall to radiation.

Yet another embodiment of the present invention may be described as a method of delivering radiation to a treatment site inside the vasculature of a patient using a gas-filled balloon catheter and a radiation source wherein the method includes the steps of: (1) inserting the catheter into the vasculature such that the balloon is adjacent to a treatment site; (2) inserting the radiation source into the catheter such that the radioactive portion is adjacent to the balloon; (3) inflating the balloon with a gas; and (4) exposing the treatment site to radiation from the radiation source through the gas in the balloon. The balloon may be inflated prior to or subsequent to inserting the radiation source. Preferably beta radiation is used, but other radioisotopes may be employed.

BRIEF DESCRIPTION OF THE DRAWINGS

FIG. 1 is a partially sectioned side view of an embodiment of the present invention.

FIG. 2 is a cross-sectional view taken at A—A in FIG. 1.

FIG. 3 is a side view of an alternative embodiment of the present invention including a helical-shaped balloon.

FIG. 6 is a partially sectioned side view of an alternative embodiment of the present invention including a perfusion lumen passing through the balloon.

FIG. 7 is a cross-sectional view taken at B—B in FIG. 6.

FIG. 8 is a cross-sectioned side view of an alternative sheath of the present invention.

DETAILED DESCRIPTION OF THE INVENTION

Figure 4:
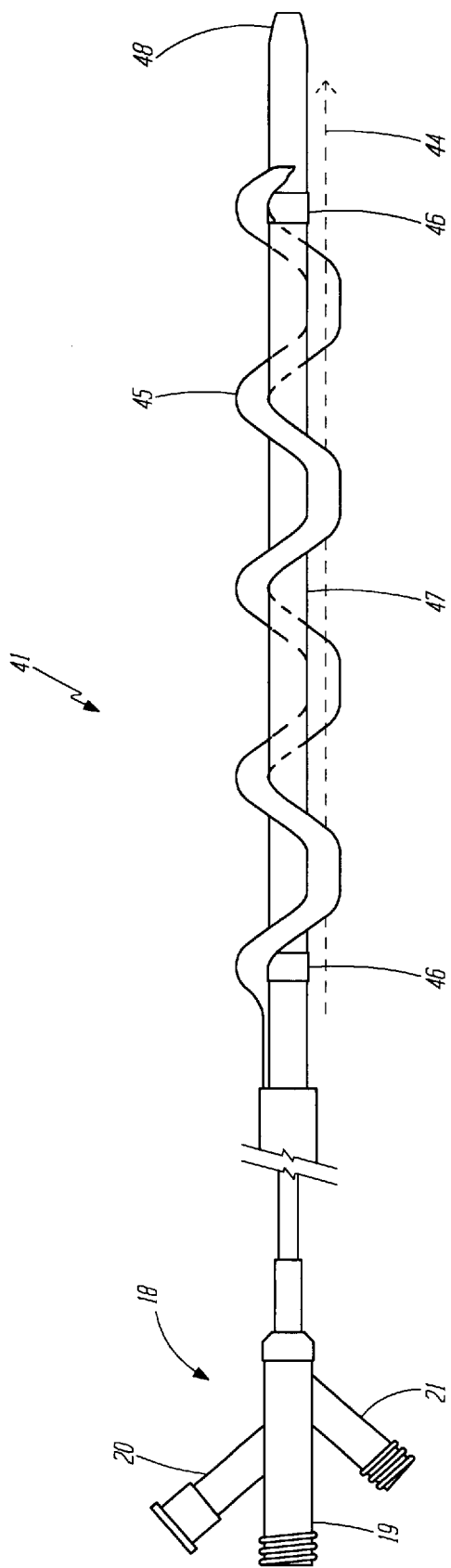
FIG. 4 is a side view of an alternative embodiment of the present invention including a toroidal-serpentine-shaped balloon.

The following detailed description should be read with reference to the drawings in which similar parts in different drawings are numbered the same. The drawings, which are not necessarily to scale, depict exemplary embodiments and are not intended to limit the scope of the invention.

Examples of suitable materials, dimensions, parts, assemblies, manufacturing processes and methods of use are described for each embodiment. Otherwise, that which is conventional in the field of the invention may be implemented. Those skilled in the field will recognize that many of the examples provided have suitable alternatives which may also be utilized.

Refer now to FIGS. 1 and 2 which illustrate a radiation delivery system 10 of the present invention. Radiation delivery system 10 includes a catheter 11 having an open-ended lumen 12 extending therethrough. A closed-ended sheath 13 surrounds a radiation source 14 (such as a guide wire) disposed in the open-ended lumen 12. An after-loader 22 may be connected to the proximal end of the radiation source 14 to advance and retract the radiation source 14 and safely contain it when not in use.

The catheter 11 includes an inflatable balloon 15 having an interior 16 which is in fluid communication with an inflation lumen 17. The catheter 11 illustrated in FIGS. 1 and 2 has a coaxial shaft construction including an inner tube 23 and an outer tube 24. Other shaft constructions may be employed such as a dual lumen shaft design illustrated in FIG. 6. A manifold 18 is connected to the proximal end of the catheter 11 and includes a guide wire port 19 and a flush port 20 both of which are in fluid communication with the open-ended lumen 12. The guide wire port may include a toughy-borst (not shown) to seal about the proximal end of the closed-end sheath 13. The manifold 18 also includes an inflation port 21 which is in fluid communication with the inflation lumen 17 and the interior 16 of the balloon 15.

The closed-end sheath 13 preferably extends to the proximal end of the catheter 11 and may include means for connection to the after-loader 22. The closed-end sheath 13 may be formed of polyethylene, PTFE coated polyimide or other suitable flexible material. The closed-end sheath 13 may have a length of about 100 to 300 cm depending on the length of the catheter 11. A wall thickness between 0.0002 and 0.005 inches is preferred to minimize profile and radiation absorption.

As included with catheter 11 illustrated in FIGS. 1 and 2, the open-ended lumen 12, closed-ended sheath 13, radiation source 14, after loader 22 and toughy-borst are also included with catheters 31, 41, 51 and 61 as illustrated in FIGS. 3, 4, 5 and 6 respectively. In addition, those skilled in the art will appreciate that the various features of each catheter 11, 31, 41, 51 and 61 may be mixed and matched depending on the desired result. For example, the rapid exchange features of catheter 51 may be incorporated into perfusion catheter 61, resulting in a perfusion rapid exchange catheter for the delivery of radiation. As another example, the centering balloon 35 or 45 may be contained inside balloon 15 of catheters 11 and 61 to provide a centering function, even in curved vasculature.

Refer now to FIGS. 3 and 4 which illustrate alternative radiation delivery catheters 31 and 41. Alternative catheters 31 and 41 may be used in place of catheter 11 for the radiation delivery system 10 illustrated in FIG. 1. Except as described herein, the design and use of alternative catheters 31 and 41 is the same as catheter 11. Alternative catheter 41 may be made as described in co-pending U.S. patent application Ser. No. 08/608,655 which is incorporated herein by reference. Similarly, alternative catheter 31 may be made as described in the above-referenced case except that the balloon 35 is wound in a helical shape rather than a serpentine shape.

With reference to FIG. 3, alternative catheter 31 includes a helically-shaped balloon 35 which is wound around the distal end of the catheter 31. When the helically-shaped balloon 35 is inflated, a helically-shaped perfusion path 36 is defined between the balloon 35, the shaft 37 and the inside surface of the blood vessel. The blood perfusion path 36 allows blood to flow across the treatment site while the balloon 35 is inflated. In addition, the concentric and flexible helical shape of the inflated balloon 35 maintains the distal portion of the catheter 31 centered in the vessel, even around turns in the vasculature. Having the catheter 31 centered in a vessel permits the uniform distribution of radiation to the treatment site.

The distal end of the shaft 37 may include a reduced diameter tip 38 with a corresponding reduced inside diameter open-ended lumen (not visible). The reduced inside diameter permits a conventional guide wire to exit out the distal end of the catheter 31 but prohibits the sheath 13 and radioactive source wire 14 from exiting. This assumes, of course, that the sheath 13 or radioactive source wire 14 is larger than the guide wire. A reduced diameter tip may be included on any of the catheters described herein.

With reference to FIG. 4, alternative catheter 41 includes a toroidal-serpentine-shaped balloon 45. When the serpentine-shaped balloon 45 is inflated, a linear perfusion path 44 is defined between the balloon 45, the shaft 47 and the inside surface of the blood vessel. The blood perfusion path 44 allows blood to flow across the treatment site while the balloon 45 is inflated. As with the helical balloon described above, the concentric and flexible serpentine shape of the inflated balloon 45 maintains the distal portion of the catheter 41 centered in the vessel, even around turns in the vasculature. Having the catheter 41 centered in a vessel permits the uniform distribution of radiation to the treatment site. A further advantage of the serpentine-shaped balloon 45 is the relative linearity of the perfusion path 44 which tends to minimize resistance to blood flow.

Catheter 41 may also include two radiopaque markers 46 to facilitate radiographic placement in the vasculature. The distal end of the shaft 47 may include a reduced diameter tip 48 with a corresponding reduced inside diameter open-ended lumen (not visible). The reduced inside diameter permits a conventional guide wire to exit out the distal end of the catheter 41 but prohibits the sheath 13 and radioactive source wire 14 from exiting.

It is also contemplated that both the helical balloon 35 and the serpentine balloon 45 may be covered with an elastomeric sleeve to aid in collapsing the balloon 35/45 upon deflation. This sleeve would be connected to the shaft adjacent the proximal and distal ends of the balloon 35/45. It is further contemplated that this sleeve may include perfusion holes both proximally and distally to permit blood perfusion along the perfusion path 36/44 defined by the balloon 35/45. If a gas is used to inflate the balloon 35/45 in large diameter vessels (e.g., peripheral vasculature), it is preferred to not permit perfusion of blood which would otherwise absorb beta radiation. In such a situation, the sleeve would not include per fusion holes.

Figure 5A:
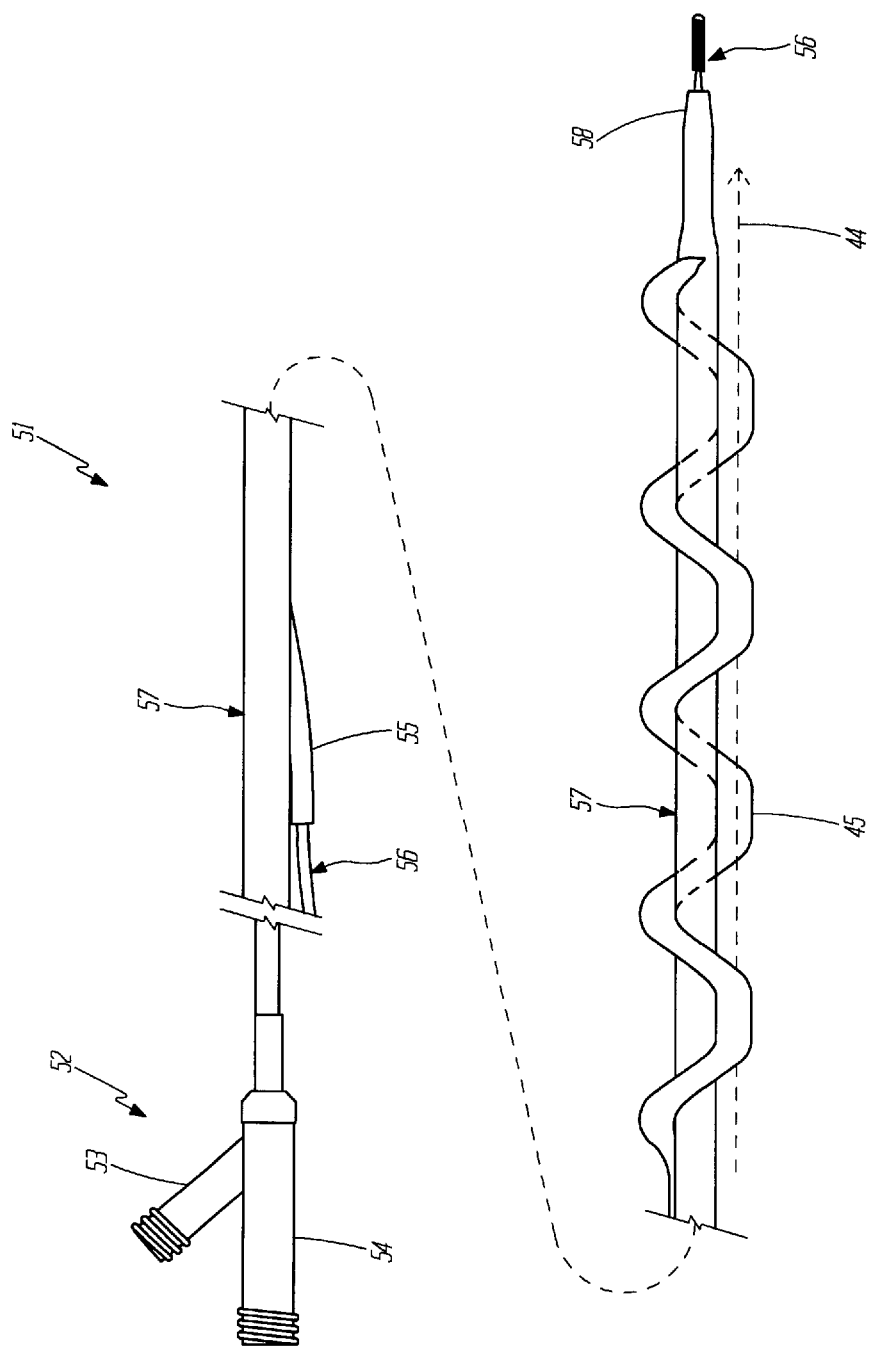
FIGS. 5a, 5b and 5c are partially sectioned side views of an alternative embodiment of the present invention including a rapid-exchange guide wire lumen.
Figure 5B:
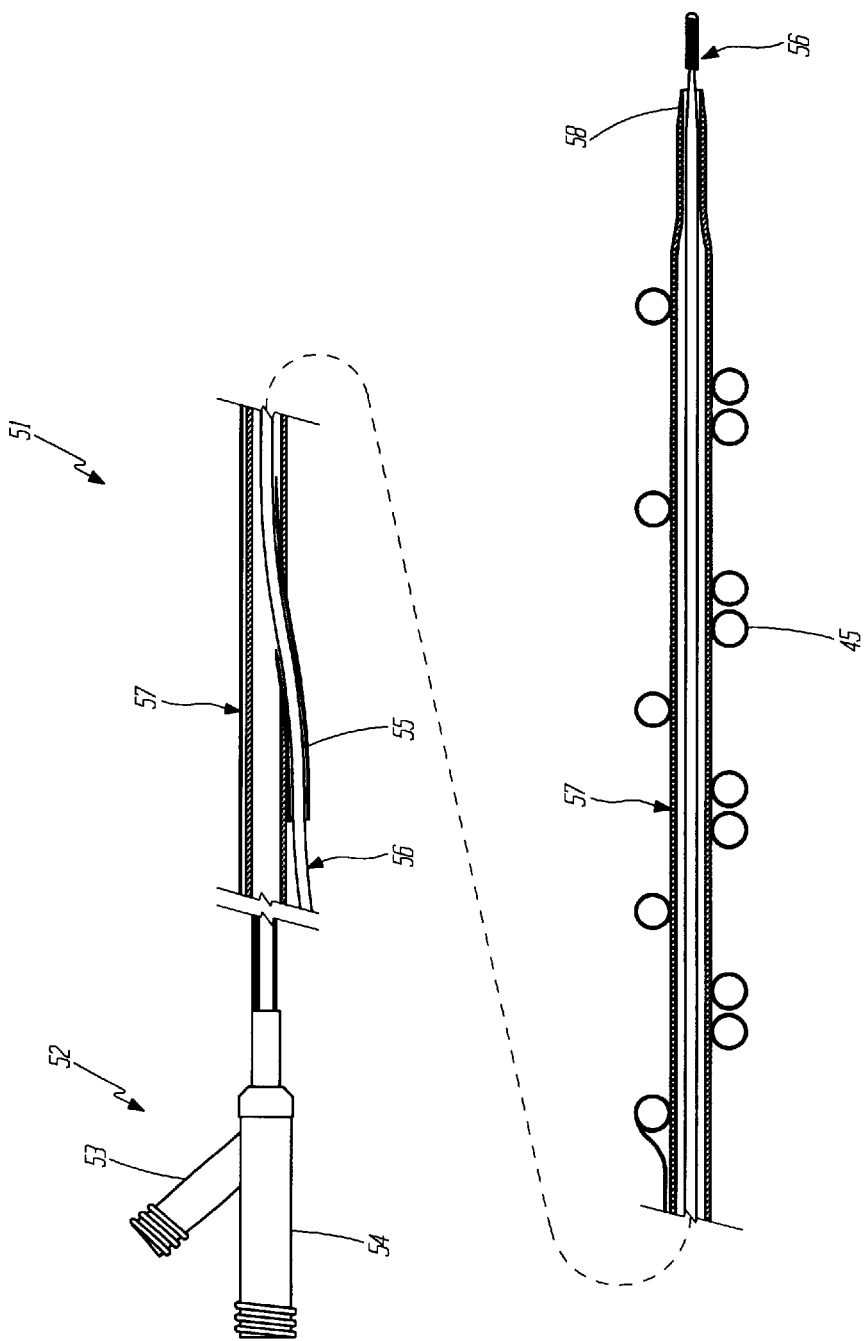
Figure 5C:
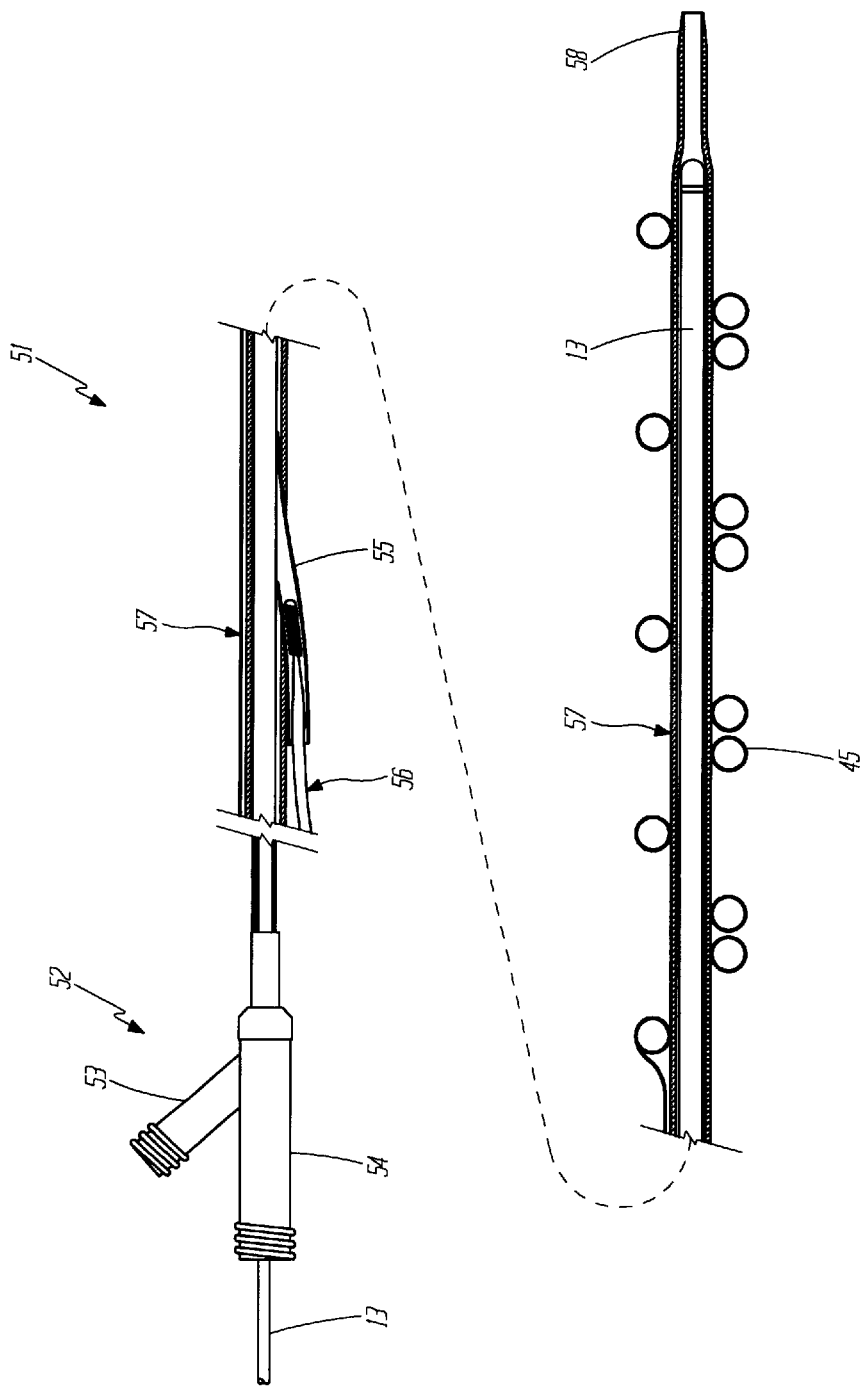

Refer now to FIGS. 5a, 5b and 5c which illustrate a rapid-exchange embodiment of the present invention. Alternative catheter 51 may be used in place of catheter 11 for the radiation delivery system 10 illustrated in FIG. 1. Except as described herein, the design and use of alternative catheter 51 is the same as catheter 11.

Rapid-exchange catheter 51 includes an elongate shaft 57 with a manifold 52 connected to the proximal end and a balloon 45 connected to the distal end. Although catheter 51 is shown with a serpentine balloon 45 and a corresponding linear perfusion path 44, any of the balloon types described herein may be used.

The manifold 52 includes a balloon inflation port 53 which is in fluid communication with the balloon 45 via a conventional inflation lumen. A radiation source entry port 54 is also included in the manifold 52. The entry port 54 communicates with the open-ended lumen and permits the insertion of the sheath 13 and radiation source 14. The open-ended lumen terminates in a reduced diameter tip 58 which permits a conventional guide wire 56 to exit out the distal end of the catheter 51 but prohibits the sheath 13 and radioactive source wire 14 from exiting.

The guide wire 56 enters the shaft 57 at the proximal guide wire tube 55. The guide wire tube 55 is located near the distal end of the catheter to permit catheter exchange without the need for an extension wire or wire trapping device. As best seen in FIG. 5c, the guide wire tube 55 has sufficient length such that the guide wire 56 may be pulled back and out of the open-ended lumen. In particular, the distance from the proximal end of the guide wire tube 55 to the distal end of the catheter 51 is less than the length of the guide wire extending outside of the patient's body. With the guide wire pulled back, the radioactive source wire 14 and the sheath 13 may be inserted into the entry port 54 to the distal end of the catheter 51.

Refer now to FIGS. 6 and 7 which illustrate an alternative perfusion catheter 61. Alternative catheter 61 may be used in place of catheter 11 for the radiation delivery system 10 illustrated in FIG. 1. Except as described herein, the design and use of alternative catheter 61 is the same as catheter 11.

Perfusion catheter 61 includes an elongate shaft 67 with a manifold 18 connected to the proximal end and a balloon 16 connected to the distal end. The shaft 67 is a multi-lumen type extrusion including an open-ended lumen 62 and an inflation lumen 63. Inflation lumen 63 provides fluid communication between the inflation port 21 and the interior of the balloon 16. Open ended lumen 62 is in communication with entry port 19 for the insertion of a guide wire (not shown) or the radioactive source 14 and sheath 13. A guide wire extension tube 64 is connected to the distal end of the multi-lumen shaft 67 and rigidly connects to the distal end of the balloon 15.

Catheter 61 includes a series of perfusion ports 65 which are in fluid communication with the distal portion of the open-ended lumen 62. The perfusion ports 65 permit blood to flow across the treatment site via the open-ended lumen while the balloon 15 is inflated.

With reference now to FIG. 8, an alternative sheath 81 is illustrated. Alternative sheath 81 may be used in place of sheath 13 for the radiation delivery system 10 illustrated in FIG. 1. Except as described herein, the design and use of alternative sheath 81 is the same as sheath 13.

Sheath 81 includes a proximal portion 82 and a distal portion 83, wherein the proximal portion 82 includes a relatively thicker wall and larger outside diameter. The thicker wall tends to absorb radiation to reduce the amount of unwanted exposure, particularly exposure of the medical personnel. The larger outside diameter of the proximal portion 84 may be used in conjunction with a corresponding restriction in the open-ended lumen 12 of any of the catheters described herein. Specifically, the leading edge or ridge 86 of the proximal portion 82 may abut a mating restriction in the open-ended lumen 12 such that the sheath 81 cannot be advanced beyond that point. The leading edge 86 and the mating restriction in the open-ended lumen serve the same function as the reduced diameter tip described previously and may be used in lieu thereof. In other words, the leading edge 86 and the mating restriction in the open-ended lumen would permit a conventional guide wire 56 to exit out the distal end of the catheter but would prohibit the sheath 81 and radioactive source wire 14 from exiting the distal end of the catheter.

The closed-end sheath 81 may include means for connection to the after-loader 22. The closed-end sheath 81 may be formed of polyethylene, PTFE coated polyimide or other suitable flexible material. The closed-end sheath 81 may have a length of about 100 to 300 cm depending on the length of the catheter 11. On the distal portion 83, a wall thickness between 0.0002 and 0.005 inches is preferred to minimize profile and radiation absorption. On the proximal portion 82, a wall thickness between 0.040 and 1.0 inches is preferred to maximize radiation absorption without significantly compromising profile. The outside diameter of the proximal portion 82 may be greater than the vascular access size on the portion of the sheath 81 that remains outside the body. Once the radiation source is inside the body, the risk of exposure of beta radiation to medical personnel in diminished.

Sheath 81 may also include a radiopaque marker 84 to facilitate radiographic placement of the sheath 81 and radioactive wire 14. Such a radiopaque marker 84 may also be included on sheath 13.

Sheath 81 may also include a series of annular magnets 85. Magnets 85 may be used to interact with a series of magnets connected to the catheter 11, 31, 41, 51 or 61 or a series of magnets connected to a guide catheter (not shown). This general arrangement is described in more detail in PCT publication WO 95/21566 which is fully incorporated herein by reference. The interacting magnets provide a means to longitudinally control and stabilize the position of the radiation source relative to the patient and treatment site.

In practice, catheters 11, 31, 41, 51 and 61 may be used to deliver radiation to the vascular wall in the following manner. After vascular access is established and a guide catheter is in position (if desired), the catheter 11/31/41/51/61 is inserted into the patient with the distal portion adjacent the treatment site. If a guide wire is used, the guide wire may be inserted prior to or simultaneously with the catheter. The balloon is then inflated to a low pressure sufficient to center the balloon in the vasculature and prevent movement of the catheter relative to the treatment site. Optionally, the balloon may first be inflated to a higher pressure in order to dilate the treatment site. If desired, the balloon may be inflated with a gas such as nitrogen, carbon dioxide or other non-toxic gas to minimize the absorption of radiation by the inflation media. After dilatation, the balloon is maintained in an inflated state, preferably at a low pressure, to center the catheter in the vascular lumen. The sheath 13 is placed over the radiation wire 14, preferably ahead of time, and the two are advanced into the open-ended lumen using an afterloader system. Optionally, the sheath 13 is first loaded into the open-ended lumen of the catheter and the proximal end of the sheath is connected to the after-loader, followed by insertion of the radioactive source wire 14. The toughy-borst is maintained sufficiently loose to allow advancement and may be locked to fully seal about the sheath 13 once the radiation wire 14 and sheath 13 are in the desired position. If a guide wire is used in the open-ended lumen, the guide wire is preferably retracted to permit passage of the radioactive wire 14 and sheath 13. If a rapid exchange catheter 51 is used, the guide wire is pulled back into the proximal guide wire tube 55. The vascular wall is then exposed to radiation (preferably beta radiation) for the desired period of time. The radioactive wire 14 and sheath 13 are removed from the catheter 11/31/41/51/61 and the catheter is removed from the patient.

While the specification describes the preferred embodiments, those skilled in the art will appreciate the spirit and scope of the invention with reference to the appended claims. Claims directed to methods of the present invention may be read without regard as to the order of the steps unless contraindicated by the teachings herein.

What is claimed is:

1. An intravascular radiation delivery system, comprising:
   a. a catheter having a proximal end, a distal end, an exterior and an open-ended lumen extending therethrough, the open-ended lumen being in fluid communication with the exterior of the catheter;
   b. an elongate radiation source having a proximal end, a distal end and a radioactive portion adjacent the distal end, the elongate radiation source disposed in the open-ended lumen of the catheter; and
   c. a closed-ended sheath disposed in the open-ended lumen of the catheter and about the elongate radiation source so as to prevent fluid communication between the radiation source and the open-ended lumen.

2. A radiation delivery system as in claim 1, wherein the catheter includes an inflatable balloon disposed about the distal end of the catheter, the balloon having an interior.

3. A radiation delivery system as in claim 2, wherein the catheter includes an inflation lumen extending therethrough, the inflation lumen communicating with the interior of the balloon.

4. A radiation delivery system as in claim 3, further comprising a guide wire, the guide wire extending through the open-ended lumen of the catheter.

5. A radiation delivery system as in claim 4, wherein the open-ended lumen extends through a portion of the length of the catheter.

6. A radiation delivery system as in claim 4, wherein the open-ended lumen extends through the entire length of the catheter.

7. A radiation delivery system as in claim 2, wherein the catheter includes a blood perfusion lumen.

8. A radiation delivery system as in claim 7, wherein the perfusion lumen extends through the balloon.

9. A radiation delivery system as in claim 2, wherein the open-ended lumen is centered in the interior of the balloon.

10. A radiation delivery system as in claim 9, wherein the balloon is helical-shaped.

11. A radiation delivery system as in claim 9, wherein the balloon is toroidal-serpentine-shaped.

12. A radiation delivery system as in claim 9, 10 or 11, wherein the catheter includes a blood perfusion lumen.

13. A radiation delivery system as in claim 12, wherein the perfusion lumen extends through the balloon.

14. A radiation delivery system as in claim 12, wherein the open-ended lumen has a reduced diameter adjacent the distal end of the catheter.

15. A radiation delivery system as in claim 14, wherein the radiation source has a distal profile and the reduced diameter of the open-ended lumen is less than the distal profile of the radiation source.

16. A method of delivering radiation to a treatment site inside the vasculature of a patient, the method comprising the steps of:
   a. providing a catheter having a proximal end, a distal end, an exterior and an open-ended lumen extending therethrough, the open-ended lumen being in fluid communication with the exterior of the catheter;
   b. providing an elongate radiation source having a proximal end, a distal end and a radioactive portion adjacent the distal end;
   c. providing a closed-end sheath;
   d. inserting the catheter into the vasculature of a patient;
   e. inserting the elongate radiation source into the closed-end sheath;
   f. inserting the radiation source and the closed-end sheath into the open-ended lumen of the catheter such that the radioactive portion is positioned adjacent a treatment site; and
   g. exposing the vascular wall to radiation from the radiation source.

17. A method of delivering radiation as in claim 16, the method further comprising the steps of:

h. removing the radiation source from the catheter; and i. removing the catheter from the patient.

18. A method of delivering radiation as in claim 16, the method further comprising the step of removing the radiation source from the catheter and the catheter from the patient at the same time.

19. A method of delivering radiation as in claim 16, the method further comprising the step of inserting the catheter into the vasculature over a guide wire.

20. A method of delivering radiation as in claim 19, the method further comprising the step of removing the guide wire from the catheter prior to exposing the vascular wall to radiation.

21. A method of delivering radiation to a treatment site inside the vasculature of a patient, the method comprising the steps of:

a. providing a catheter having a distal end and a balloon mounted on the distal end and an open ended lumen extending along the catheter;

b. providing a radiation source having a distal end and a radioactive portion adjacent to the distal end;

c. providing a closed-end sheath;

d. inserting the catheter in the vasculature of a patient such that the balloon is adjacent to a treatment site;

e. inserting the closed-end sheath into the open-ended lumen of the catheter;

f. inserting the radiation source into the closed-end sheath such that the radioactive portion is adjacent to the balloon;

g. inflating the balloon with a gas;

h. exposing the treatment site to radiation from the radiation source through the gas in the balloon.

22. A method of delivering radiation as in claim 21, wherein the radioactive source emits a beta isotope.

23. A method of delivering radiation as in claim 22, the method further comprising the step of inflating the balloon prior to inserting the radiation source.

24. A method of delivering radiation as in claim 22, the method further comprising the step of inflating the balloon subsequent to inserting the radiation source.

25. An intravascular radiation delivery system as in claim 1 wherein the closed-end sheath has a thicker wall proximal portion relative to a thinner wall distal portion such that the proximal portion shields radiation before the radiation source is positioned inside the patient.

26. An intravascular radiation delivery system as in claim 1 wherein the closed-end sheath has a ridge or edge at a point proximal of the distal end of the sheath to prohibit the sheath from exiting the catheter.

27. A method of delivering radiation to a treatment site inside the vasculature of a patient, the method comprising the steps of:

a. providing a catheter having a proximal end, a distal end, an exterior and an open-ended lumen extending therethrough, the open-ended lumen being in fluid communication with the exterior of the catheter;

b. providing an elongate radiation source having a proximal end, a distal end and. a radioactive portion adjacent the distal end;

c. providing a closed-end sheath;

d. inserting the catheter into the vasculature of a patient;

e. inserting the closed-end sheath into the open-ended lumen of the catheter;

f. inserting the radiation source into the sheath such that the radioactive portion is positioned adjacent a treatment site; and g. exposing the vascular wall to radiation front the radiation source.

28. A method of delivering radiation as in claim 27, the method further comprising the steps of:

h. removing the radiation source from the sheath; and i. removing the sheath from the catheter.

29. A method of delivering radiation as in claim 28, the method further comprising the step of:

j. removing the catheter from the patient.

30. A method of delivering radiation as in claim 27, the method further comprising the step of inserting the catheter into the vasculature over a guide wire.

31. A method of delivering radiation as in claim 30, the method further comprising the step of removing the guide wire from the catheter prior to exposing the vascular wall to radiation.

32. A method of delivering radiation as in claim 29, the method further comprising the step of removing the catheter from the patient over a guide wire.

* * * * *

UNITED STATES PATENT AND TRADEMARK OFFICE
CERTIFICATE OF CORRECTION

PATENT NO.     : 6,234,951 B1
DATED          : May 22, 2001
INVENTOR(S)    : Roger N. Hastings Page 1 of 1

It is certified that error appears in the above-identified patent and that said Letters Patent is hereby corrected as shown below:

Column 10,
Line 15, after "and" and before "a", delete "."
Line 24, delete "front" and insert -- from --.

Signed and Sealed this

Twenty-first Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,234,951 B1
DATED : May 22, 2001
INVENTOR(S) : R.N. Hastings et al.

It is certified that error appears in the above-identified patent and that said Letters Patent is hereby corrected as shown below:

<u>Title page,</u>
Item [12], "Hastings" should read -- Hastings et al. --.
Item [75], "Inventor: Roger N. Hastings, Maple Grove, MN (US)" should read
-- Inventors: Roger N. Hastings, Maple Grove, MN (US); Thomas R. Hektner, Medina, MN (US); Stewart M. Kume, Belmont, CA, (US) --

Signed and Sealed this

Fifteenth Day of June, 2004

JON W. DUDAS
*Acting Director of the United States Patent and Trademark Office*